(12) United States Patent
Ananthanarayanan et al.

(10) Patent No.: US 12,083,276 B2
(45) Date of Patent: Sep. 10, 2024

(54) TRACHEAL INTUBATION FACILITATOR WITH SUPERIOR VENTILATING CAPABILITY

(71) Applicants: Kalyanaraman Ananthanarayanan, Maharashtra (IN); Ashish Patyal, New Delhi (IN); Nirav Kotak, New Delhi (IN)

(72) Inventors: Kalyanaraman Ananthanarayanan, Maharashtra (IN); Ashish Patyal, New Delhi (IN); Nirav Kotak, New Delhi (IN)

( * ) Notice: Subject to any disclaimer, the term of this patent is extended or adjusted under 35 U.S.C. 154(b) by 378 days.

(21) Appl. No.: 16/955,799

(22) PCT Filed: Apr. 4, 2018

(86) PCT No.: PCT/IN2018/050192
§ 371 (c)(1),
(2) Date: Jun. 19, 2020

(87) PCT Pub. No.: WO2019/123474
PCT Pub. Date: Jun. 27, 2019

(65) Prior Publication Data
US 2020/0338291 A1 Oct. 29, 2020

(30) Foreign Application Priority Data
Dec. 22, 2017 (IN) .............................. 201721046391

(51) Int. Cl.
*A61M 16/04* (2006.01)
*A61B 1/267* (2006.01)
*A61M 25/01* (2006.01)

(52) U.S. Cl.
CPC .... *A61M 16/0488* (2013.01); *A61M 16/0434* (2013.01); *A61M 25/0102* (2013.01);
(Continued)

(58) Field of Classification Search
CPC .......... A61M 16/0488; A61M 16/0452; A61M 16/0434; A61M 2025/0008;
(Continued)

(56) References Cited

U.S. PATENT DOCUMENTS 4,512,765 A 4/1985 Muto
5,499,625 A * 3/1996 Frass ..................... A61M 16/04
128/207.14
(Continued)

FOREIGN PATENT DOCUMENTS

GB 1113484 A * 5/1968
GB 2507474 A 5/2014
(Continued)

OTHER PUBLICATIONS

Foreign Communication from a Related Counterpart Application, International Search Report and Written Opinion dated Jul. 26, 2018, International Application No. PCT/IN2018/050192 filed on Apr. 4, 2018.
(Continued)

*Primary Examiner* — Daniel J Colilla
(74) *Attorney, Agent, or Firm* — Conley Rose, P.C.; Michael W. Piper; Elexis A. Jones

(57) ABSTRACT

We describe a Tracheal Tube insertion facilitator ("modified bougie") with superior ventilating capability to enable medical/paramedical personnel to place tracheal/bronchial tubes reliably in trachea/bronchus of the patients under anaesthesia or patients in respiratory distress, and provide respiratory support. This device is particularly useful in situations where the conventional tracheal intubation technique using a laryngoscope is difficult or near impossible. This device has a outer cylindrical member, inner hollow stylet and a dynamic cuff which inflates during Positive Pressure Ventilation/Jet ventilation, and hence enabling oxygenation in patients with
(Continued)

respiratory distress even before the tracheal tube is inserted into the patient's airway.

10 Claims, 6 Drawing Sheets

(52) U.S. Cl.
CPC .... *A61B 1/2676* (2013.01); *A61M 2205/6063* (2013.01); *A61M 2205/6081* (2013.01); *A61M 2210/1032* (2013.01); *A61M 2210/1035* (2013.01); *A61M 2210/105* (2013.01)

(58) Field of Classification Search
CPC .... A61M 2025/6081; A61M 2205/584; A61B 1/2676
See application file for complete search history.

(56) References Cited

U.S. PATENT DOCUMENTS

| | | | |
|---|---|---|---|
| 5,638,813 A * | 6/1997 | Augustine | A61M 16/04 128/207.15 |
| 9,956,367 B1 * | 5/2018 | Sun | A61B 1/00082 |
| 2003/0121521 A1 * | 7/2003 | Hipolito | A61M 16/04 128/207.14 |
| 2005/0081861 A1 | 4/2005 | Nasir | |
| 2005/0224079 A1 * | 10/2005 | Green | A61M 16/04 128/207.14 |
| 2006/0081253 A1 | 4/2006 | Nelson | |
| 2006/0157060 A1 * | 7/2006 | Nelson | A61M 16/0418 128/207.14 |
| 2006/0207604 A1 * | 9/2006 | Nelson | A61M 16/0443 128/207.14 |
| 2008/0017195 A1 * | 1/2008 | Yoshida | A61M 16/0418 128/200.26 |
| 2008/0066746 A1 | 3/2008 | Nelson et al. | |
| 2010/0307489 A1 | 12/2010 | Harms et al. | |
| 2015/0126908 A1 | 5/2015 | Azagury et al. | |
| 2015/0290414 A1 * | 10/2015 | Vasan | A61B 1/00032 128/200.26 |
| 2017/0209022 A1 | 7/2017 | Molnar | |
| 2020/0297957 A1 * | 9/2020 | Poormand | A61M 16/0418 |

FOREIGN PATENT DOCUMENTS

| | | |
|---|---|---|
| WO | 99/66975 A1 | 12/1999 |
| WO | 2008/033486 A2 | 3/2008 |

OTHER PUBLICATIONS

Foreign Communication from a Related Counterpart Application, Extended European Search Report dated Aug. 10, 2021, European Application No. 18891861.

Smale JR1, Kutty K, Ohlert J, Cotter T, Endotracheal intubation by paramedics during in-hospital CPR, Chest 1995, June; 107(6): pp. 1655-1661.

Gottlieb M1, Sharma V2, FieldJ 3, Rozum M4, Bailitz J3; Utilization of a gum elastic bougie to facilitate single lung intubation. American Journal of Emergency Medicine. Dec. 2016; 34(12): pp. 2408-2410. Doi: 10.1016/j.ajem.2016.08.057 Epub Aug. 27, 2016.

* cited by examiner

TRACHEAL INTUBATION FACILITATOR WITH SUPERIOR VENTILATING CAPABILITY

FIELD OF INVENTION

The present invention discloses a medical airway device, more specifically a modified Tracheal Tube Insertion Facilitator ("modified Bougie") with superior ventilating capability to aid the placement of tracheal/bronchial tubes in the airway of patients, particularly the ones which are difficult with conventional laryngoscopy aided intubation technique. This device is characterized by a outer cylindrical member, a dynamic cuff which inflates with Positive Pressure Ventilation (PPV), a ventilating stylet, a flexible tip, and a colour coded and calibrated body which is suitable for facilitating insertion of an endotracheal/endobronchial tube into the airway of a person while simultaneously providing effective ventilation to the lungs.

BACKGROUND AND PRIOR ART OF INVENTION

This device has its application in patients who are unconscious or under general anaesthesia, who have inadequate or absent respiratory efforts. In emergency medical management of a patient who is unresponsive or with inadequate respiratory efforts, 'assisted ventilation' has to be started at the earliest. This assisted ventilation is also known as 'Positive Pressure Ventilation' and this can be delivered at the level of upper airway (from nose/mouth till vocal cords) by using a 'face mask' or one of the various 'supraglottic devices' or at the level of lower airway (trachea and bronchi) by inserting a tracheal tube into the trachea of the patient.

It is necessary that the assisted ventilation of a patient under anaesthesia or respiratory distress is initiated with a minimal time lag as lack of oxygen supply for a few minutes can be fatal for most patients. Also, 'securing' the airway in unconscious patients is essential to prevent the patients stomach contents getting aspirated into the lungs resulting in a life threatening complication 'aspiration pneumonitis'. "Intubation" of the trachea with an airway tube, such as endotracheal tube (ETT, "tracheal tube") and delivering Positive Pressure Ventilation (PPV) through the same is a common method of ensuring oxygenation, preventing aspiration of gastric contents into the lungs, and administering gaseous medications. Through a properly placed airway (tracheal) tube, air or oxygen can be delivered to the patient in an emergency situation.

Laryngoscopes and E are the commonly used instruments to establish emergency tracheal tube insertion ("tracheal intubation"). But as many as 5-10% of the patients requiring emergency intubation have various associated airway abnormalities which makes the intubation difficult. Difficulty in intubation is commonly associated with obesity, pregnancy, facial trauma/abnormalities, short thick neck, laryngeal edema etc. When such an abnormality is associated with decreased respiratory reserve, routine intubation procedures may become difficult or even risky, leading to desaturation and cardiac arrest.

Normally during ideal intubating conditions, the laryngoscope will enable adequate visualization of vocal cords, enabling tracheal intubation. But in 5-10% of patients, vocal cords are not visualised or incompletely visualised due to their anterior placement, making it difficult or impossible to intubate with a normal tracheal tube.

In such situations, the emergency physician/anaesthesiologist may utilize a "Gum Elastic Bougie" ("Bougie", existing design) to facilitate tracheal intubation. A bougie is essentially a thin elongated member with an anteriorly curved distal tip that is inserted into the patient's trachea under laryngoscopy, and an ETT is advanced over the proximal end of the bougie and into the patient's trachea, using the bougie as a conduit ('railroading'). At that point, the bougie may be removed and patients 'ventilation' (Positive Pressure Ventilation, PPV) begun through the tracheal tube.

Use of a ventilating bougie is known for guiding insertion of various instruments into a passageway in a patient's body, primarily the trachea, and simultaneously providing oxygenation thereby minimizing the time lag in oxygenation which would have resulted otherwise. In many emergency situations it is necessary to intubate a patient as quickly as possible to provide a secure airway to the patient's lungs or permit Positive Pressure Ventilation (PPV).

Reference can be made to the work of. Stefans, C. Chris, W. Trevor, R. Lee. United states patent number (US 20100307489 A1) who made a bougie device for guiding insertion of an endotracheal tube into an airway of a person, comprises an elongate body of shape memory and self-lubricating material, for example Teflon. Accordingly, no lubrication is required for insertion into the airway for ease of cleaning and sterilizing for reuse. Also, the amount of curvature of the overall rod as well as an angle of the tip of the rod can be adjusted due to the shape memory characteristics of the body to accommodate a particular patent's airway. The body can also be suitably sized to have vibration transmission characteristics such that a contact with one end of the bougie device with tracheal rings of the patient can be felt by a user.

During bougie guided intubation the passage of ETT over the bougie into the trachea may take a considerable time and may often requires multiple attempts, during which the patients will exhaust his oxygen reserves and often the bougie needs to be removed and the patient ventilated with face mask.

This exposes the patients to
1) The risk associated with mask ventilation like pulmonary aspiration of gastric contents (a life threatening condition).
2) Risk associated with repeated laryngoscopy attempts, like oral trauma, breakage of teeth, myocardial ischaemia in coronary artery disease, increased trauma to airways or vocal cords or increased airway edema.
3) Risks associated with desaturation like cardiac arrest or permanent brain damage.

Also during intubation, the available "ventilating bougie's are not capable of providing effective ventilation of the lungs because most of the air is lost through the nasal and oral routes as they are the path of least resistance instead of going to the lungs. Hence chances of hypoxia increase.

Additionally, another problem with the previously known bougies is the lack of confirmation of the tracheal placement of the distal end of the bougie. If the ETT is mistakenly placed in the patient's oesophagus, subsequent ventilation may be ineffective, leading to asphyxiation.

As these bougies'" (which are available in the market) tip are bent hence angle of curvature cannot be changed during the laryngoscopy therefore if the bent bougie tip does not enter inside the laryngeal cavity, it has to be removed and bent at a more appropriate angle for reinsertion, resulting in multiple attempts, which increases apnoea time and causes hypoxia, resulting into haemodynamic disturbances.

Lung surgeries require 'lung isolation' and One Lung Ventilation (OLV) for which specially designed tubes (Double Lumen Tubes (DLT), Endobronchial tubes) need to be placed in the bronchi. In these situations, confirmation of proper placement of the bronchial tube is difficult and is often achieved by auscultation/bronchoscopy. This results in multiple attempts.

SUMMARY OF THE INVENTION

To overcome all these lacunae in the existing design, we have designed a new tracheal tube insertion facilitator (modified bougie) with a "dynamic" cuff which gets inflated only during positive pressure ventilation/jet ventilation and deflates during expiration. By doing this, the Oxygen/air provided by the positive pressure ventilation/jet ventilation can not escape from the mouth/nose and will enter the lungs and oxygenate the patient efficiently. During the expiration, since the dynamic cuff gets deflated, the expired gases can escape from the lungs around the bougie into the atmosphere.

The bougie has cylindrical outer member made of semi rigid but atraumatic material like PVC/Teflon or any other suitable material. The cylindrical outer member has two ends, a proximal end and a distal end. The proximal end has a universal adapter enabling Positive Pressure Ventilation (PPV) when connected to an anaesthesia circuit or a AMBU or a similar resuscitator. The distal end of the cylindrical outer member ends in the distal tip which is angulated anteriorly. At a short distance from the distal tip lies the Dynamic Cuff whose inner surface is fluidly communicating with the inner lumen of the outer cylindrical member through multiple apertures of suitable number and size ("inflation ports"). Between the distal tip of the outer cylindrical member and the dynamic cuff, on the body of the outer cylindrical member as described above, may lie one or more small apertures which fluidly communicate between the inner lumen of the cylindrical outer member and the outside ("ventilation ports"). These ports may help in ventilating the trachea or the contralateral bronchus when the tip of the 'bougie' lies in one bronchus.

Inside the outer cylindrical member lies the inner hollow cylindrical 'stylet' which is preferably made of metal like stainless steel or any such suitable material to provide structural rigidity and durability. The stylet has a proximal end, a distal end, an outer surface and a inner lumen. The proximal end of the stylet has an adapter to enable ventilation with jet ventilation devices. The distal tip of the stylet, when in situ, extends till the point of forward angulation of the outer cylindrical member. Just proximal to the distal tip, juxtaposing the 'inflation ports' of the outer cylindrical member, lie multiple 'inflation stylet ports' which are apertures which communicate the inner lumen of the stylet fluidly with the outer environment, which here, is the inner lumen of the outer cylindrical member, thereby inflating the Dynamic cuff while providing Jet Ventilation into the lungs.

The length of the outer cylindrical member from the distal tip till the proximal end will be approximately 65 cms. The entire length is divided into two portions, the "distal portion" and the "proximal portion". The distal portion, which begins from the distal tip, extends till 35 cms towards the proximal end of the external surface of the outer cylindrical member, is designated longitudinally into a 'right half' and a 'left half' and each half is given a contrasting colour, Eg: Blue for the left half and yellow for the right half. The "proximal portion", which begins from the 35 cm mark and extends all the way till the proximal end of the outer cylindrical member is given another contrasting color or suitable pattern/texture/markings, Eg: this proximal end will have a distinct color like red/black, or a pattern of colours or a separate texture, preferably but not limited to a rough finish. These 'colour/texture coding' system will help us to identify whether the distal tip is entering the trachea or the oesophagus and determine accurately the bronchus the distal tip is entering in case of endobronchial intubation, thereby enabling accurate placement of endobronchial tubes to facilitate Lung Isolation and One Lung Ventilation (OLV). For eg: if the left half of the modified bougie is coloured blue and the right half is coloured yellow from the proximal end till the distal tip, if the distal tip enters the Right bronchus, the bougie will get rotated towards the tight side, thereby bringing the Blue half of the outer member facing upwards at the level of the oral cavity/lips and vice versa. Once we are sure about the accurate placement of the distal tip of the outer cylindrical member in the desired bronchus, the operator may railroad the endobronchial tube into the desired bronchus or confirm the endobronchial placement of the tip further, by Positive Pressure ventilation from the proximal end of the outer cylindrical member and confirm the air entry in the desired bronchus via auscultation with a stethoscope.

If the distal tip of the bougie enters the trachea, the bougie will generally encounter resistance at the bronchus level and can not reach a depth of more than 35 cms are the level of the oral cavity/lips. After the insertion of the bougie under laryngoscopy, if the operator is able to push the bougie beyond the 35 cm mark, then he will see the black/red colour or the change of texture at the level of the lips, which will indicate that the tube has not entered the trachea but has entered the oesophagus instead. This system will make the operator realize and detect oesophageal insertion of the device in real time, without having to railroad a tracheal tube and start ventilation to confirm the oesophageal placement of the tracheal tube. This can be life saving in difficult airway situations.

The entire outer cylindrical member of the bougie will be calibrated in suitable units (cms or inches) from the distal tip all the way till the proximal end. This will help the operator to identify whether the distal tip is lying in the trachea (15-25 cms at the level of the lips), the bronchus (25-35 cms) or the oesophagus (more than 40 cms at the level of the lips) giving a rough confirmation of whether the bougie is in the airway or not. This will be very beneficial in difficult airway situations and in desaturating patients.

In its proximal end, the outer cylindrical member can be connected to the anaesthesia circuit/AMBU resuscitator or a jet ventilation device by means of a specialized "connector". These connectors differ from the standard "universal connectors" in that the distal end of the specialized connector envelope the proximal end of the outer cylindrical member from the outside, and not fit in the lumen of the outer cylindrical member (conventional design). Two specialized connectors may be provided with the device, one with a wider proximal end with 15 mm diameter, which can be used with anaesthesia circuits and AMBU resuscitator. The other specialised connector will have a narrower proximal end, of 5-6 mm diameter, which can be used with a jet ventilation device.

In another embodiment of this device, the distal tip of the outer cylindrical member is flexible and has an inbuilt mechanism, preferable but not restricted to a string based system which can be operated from the proximal end with a knob or other similar piece of equipment, to flex or extend the distal tip while manoeuvring through the airway of the patient.

In another embodiment of the device, either the outer cylindrical member or the inner stylet can house a fiberoptic bundle or any suitable visualising mechanism not restricted to a video camera, which when connected to a viewfinder/monitor to enable visualization and confirmation of the correct placement of the bougie/tracheal tube in the desired location (trachea, bronchus or any similar hollow organ)

Advantages of this Invention

1. In cases of difficult airway this is an alternative way of maintaining the oxygenation and removing carbon dioxide from the lungs even without tracheal intubation.
2. Under laryngoscopy, intubation can be done using this modified bougie even without visualising the vocal cords, and the tracheal placement of the device can be confirmed by auscultating the chest during ventilation and by feeling the grating sensation of the tracheal rings while inserting the bougie inside the trachea. Both these will be absent if the bougie is inserted into the oesophagus. Moreover, if the device is inserted accidentally into the oesophagus, the operator will be able to push it beyond 35 cm mark at the level of the lips resulting in the colour/texture change as discussed, thereby making the operator instantly aware that the 'bougie' is in the oesophagus.
3. It helps in exchanging an existing tracheal tube with a new tube without the need of laryngoscopy.
4. The distal flexible tip helps in guiding the ETT in any difficult airway where the larynx is placed anteriorly, as the distal tip can be bent while the modified bougie is still lying in the patient's airway. This eliminates the need for multiple intubation attempts.
5. Hypoxia will not occur even if facilitating the tracheal tube over the modified bougie ('railroading'), into the trachea takes time or is difficult.
6. The dynamic inflatable cuff helps in preventing the backflow of the air through mouth or nose during Positive Pressure Ventilation (PPV)/Jet Ventilation, hence maximum amount of air goes into the lung for respiration.
7. The dynamic inflatable cuff gets deflated during the process of expiration hence no hindrance to the flow of expired air so no build up of pressure inside the lungs there no barotrauma (lung injury due to pressure build up)
8. The body has vibratory transmission properties such that contact between one end of the body with tracheal rings in the airway of the person can be felt by a user contacting the opposing end of the body while inserting the bougie device into the airway;
9. Helps in accurate placement of double lumen tubes and bronchial tubes
10. Helps in Bronchial suctioning, bronchial lavage, without the need for a bronchoscope
11. Accurate placement of the tracheal/bronchial tube can be confirmed by inserting a fiberoptic scope through the lumen of the device (after removing the stylet)
12. It can be used in cardiac arrest patient for cardiopulmonary resuscitation.
13. It is very economical and can be used multi pie times.
14. Different sizes are available which permits it to be used in any age group.

OBJECTS OF THE INVENTION

The main object of this invention is to give a Tracheal Tube Insertion Facilitator ('modified bougie') to ensure adequate oxygenation during difficulty in tracheal intubation.

Another object of this invention is to ensure adequate oxygenation and removal of carbon di oxide from the lungs.

Still another object of this invention is to enable confirmation of tracheal placement of the 'bougie' by auscultation of the chest during positive pressure ventilation (PPV).

Yet another object is to give a modified bougie which helps in exchanging an existing tracheal tube with a new tube without the need of laryngoscopy Still another object is to provide tracheal tube introducer with a flexible distal tip, which can be maneuverer while attempting intubation, so that difficult intubations can be made easier.

Another object is to give a modified ventilation bougie where its body has vibratory transmission properties such that contact between the distal end of the body with tracheal rings in the airway of the person can be felt by a user holding the proximal end of the body while inserting the bougie device into the airway.

Another object is to give a modified bougie where chances of reinsertion, hypoxia and hyperdynamic response are minimized.

Further object is to give a modified bougie with a system enabling proper bronchial placement of Double lumen tubes (DLT)/Bronchial tubes by using a colour/texture coding system.

Further object is to give a modified bougie with a system to detect accidental oesophageal insertion of the device by using a colour/texture coding system.

Yet further object of the modified bougie is to enable tracheal/bronchial suction and lavage through the lumen of the introducer ("bougie")

Still further object of the modified bougie is to enable fiberoptic bronchosopy either through its lumen or through an inbuilt mechanism.

A still further object of the device is to provide a modified bougie with a specialized connector which fits on the proximal end of the outer cylindrical member from outside.

Still further object is to give a modified ventilation bougie which can be used in any age group. Yet further object is to give a cost effective modified bougie by making it reusable.

DETAILED DESCRIPTION OF INVENTION

FIG. 1 is a longitudinal section of the Tracheal Tube Insertion Facilitator ('modified bougie'). It shows the different component of the apparatus which consists of body (1), dynamic inflatable cuff (2), bougie inflation ports (3), bougie ventilation ports (4), distal bougie tip (5), hollow stylet (6), dual purpose stylet inflation/ventilation ports (7), stylet distal tip (8), universal connector (9).

Further diagrams explain each component of the Bougie in detail.

FIG. 2 shows the bougie's ventilation ports (4), distal tip of the bougie (5), distal tip of the stylet (8). The two ventilation ports (4) lies on the lateral aspects of the bougie, in between the distal tip and the dynamic cuff and are in connection with the bougie lumen for the purpose of ventilation. The distal bougie tip (5), is bent forward with an angle of about 45 degrees. The stylet's distal tip (8) helps in ventilation during dire emergency situations where stylet can directly be attached to a jet ventilation device.

FIG. 3 shows the body (1), dynamic cuff (2), bougie inflation port (3), dual purpose stylet inflation/ventilation port (7), stylet (6). The body (1) can be made up of plastic or silicon or PVC or any suitable material and acts as a channel for inspiration and expiration of the air/oxygen. The body is malleable and can be bend with force and non kinkable. It has vibratory transmission properties such that when the distal tip comes into contact with tracheal rings and when moved over the rings, grating sensation is felt at the proximal end.

The dynamic cuff (2), can be made up of silicone, rubber, polythene or any suitable material. This dynamic cuff inflates during inspiration so that the sides of the cuff come into contact with tracheal mucosa, creating the seal so that the air/oxygen delivered through AMBU bag/ventilation circuit will be delivered into the bronchial tree, preventing the leak through nose and mouth during inspiration. This cuff deflates during expiration leading to easy escape of expired gases through the nasal and oral cavity.

The multiple inflation ports (3), which lies within the tube lumen, communicate into the lumen of the dynamic cuff and, helps in inflation of dynamic cuff during inspiration. Since the luminal pressure falls during deflation of the AMBU bag/Ventilation circuit, the dynamic cuff collapses and allows the expiration to begin, enabling the exhaled air to escape through the sides of the cuff, into the oral cavity and nostrils.

The stylet has side ports (7) coinciding with the inflation ports (3) on the body of the apparatus. These ports help in inflating the dynamic cuff when the stylet is used to ventilate using a jet ventilation device ('venturi') during emergency situations.

The dual purpose stylet inflation/ventilation port (7), helps in inflation of the dynamic cuff as well as ventilation through it. Hence its dual purpose helps in preventing air leak by inflating the dynamic cuff as well as helps in ventilating the patient's lungs.

The stylet (6) is made up of a suitable metal and beside serving its purpose of ventilation it also gives strength to the bougie.

FIG. 4 shows tube body (1), universal connector (9), stylet (6). The 15 mm standard universal connector (9), is made up of hard plastic and connects to the body for the ventilation purpose.

Next five figures show the working of the apparatus as a whole.

Figure 8:
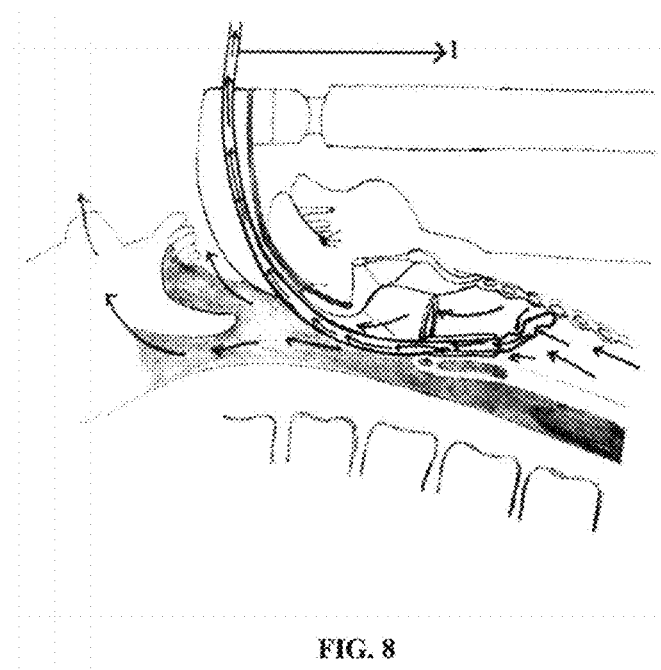

FIG. 8 shows the modified bougie in the patient's airway which is put through the mouth, wherein the dynamic cuff lies inside the trachea, and deflates during expiration. Hence the expired gases exits through two channels one through the natural airway (sides of the bougie—mouth/nostrils) and other through the lumen of the bougie. This results in complete expiration with no residual expired gas left behind or getting trapped, thereby preventing barotrauma to lungs.

Figure 9:
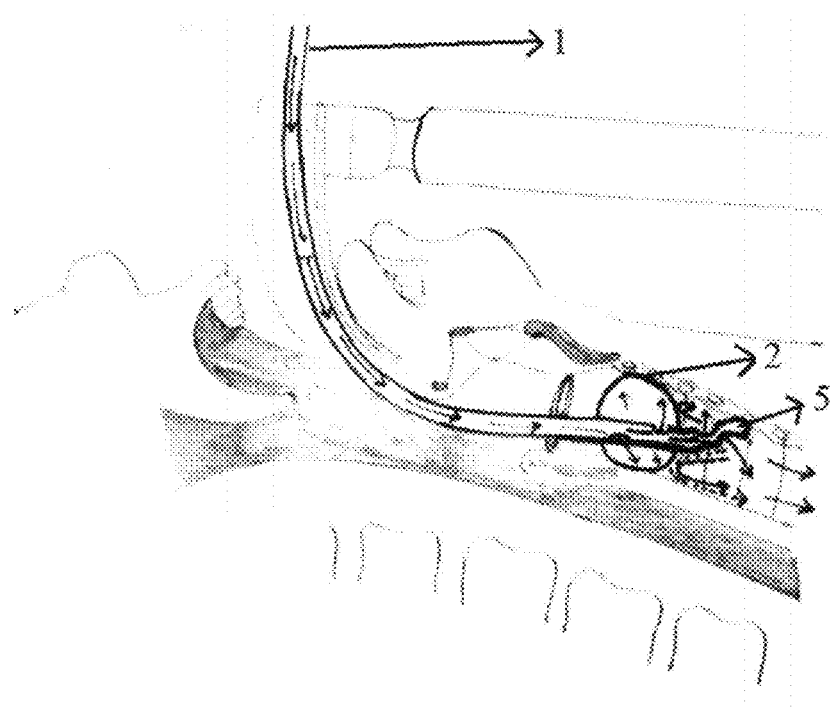

FIG. 9 shows the modified bougie in the patient's airway, which is put through the mouth, wherein the dynamic cuff lies inside the trachea, which inflates during inspiration and helps in sealing the trachea from within thereby helps in preventing the backflow of the air through the mouth or nose during the inspiration, hence maximum amount of air goes into the lung for respiration which helps in proper ventilation of the lungs. Different sizes are available which can be used in patients of variable age.

Figure 1:
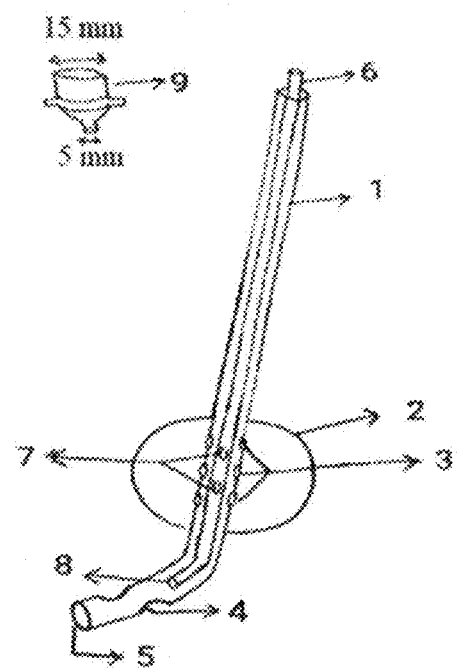
Figure 2:
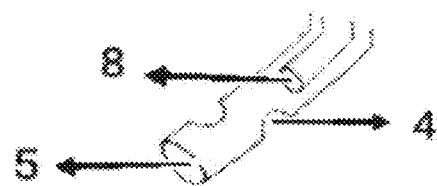
Figure 3:
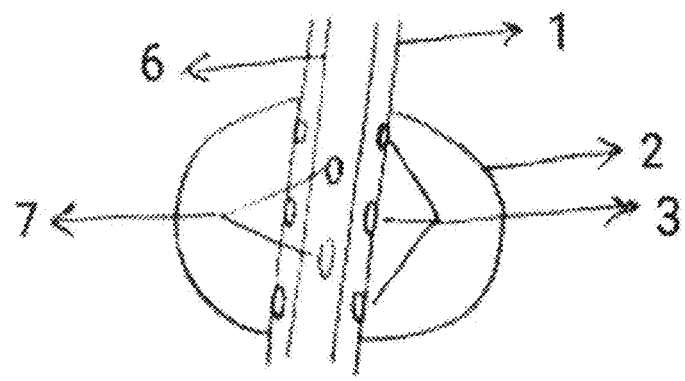
Figure 4:
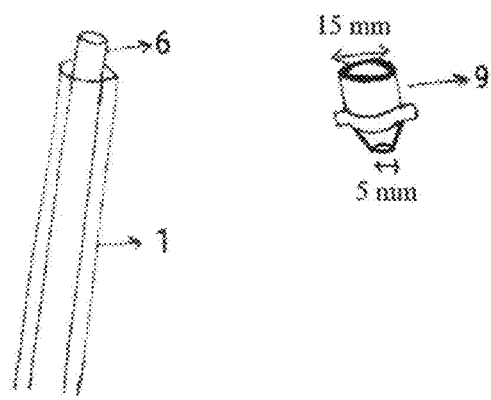
Figure 5:
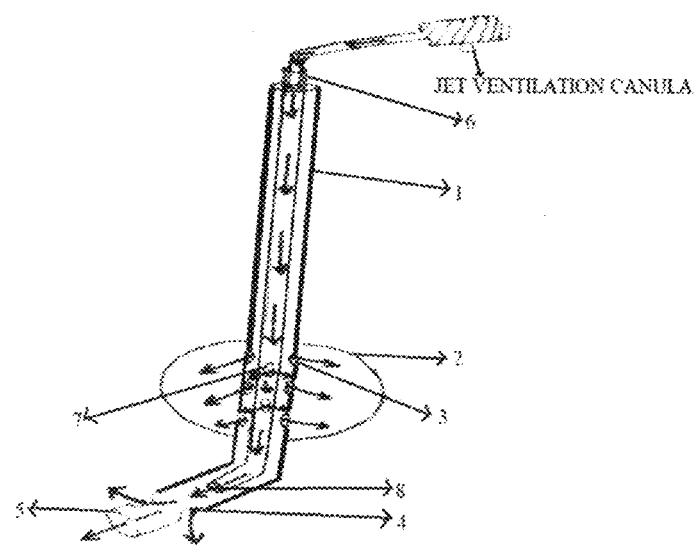
FIG. 5 shows the inflation of the dynamic cuff during the inspiration when the stylet is inside the bougie and stylet proximal end is connected to the jet ventilation cannula.
Figure 6:
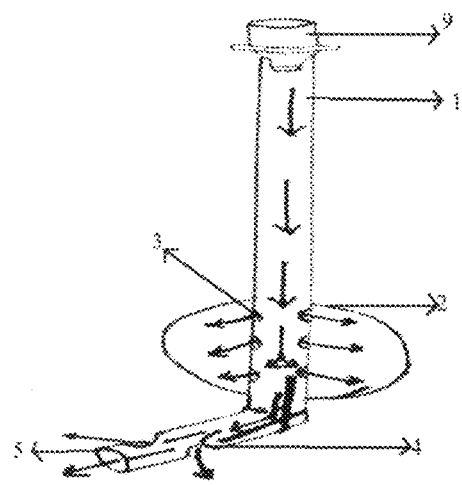
FIG. 6 shows the inflation of the dynamic cuff during the inspiration when the stylet is not there and the bougie is connected to the universal connector which can be connected to the ambu bag or any oxygen tubings.
Figure 7:
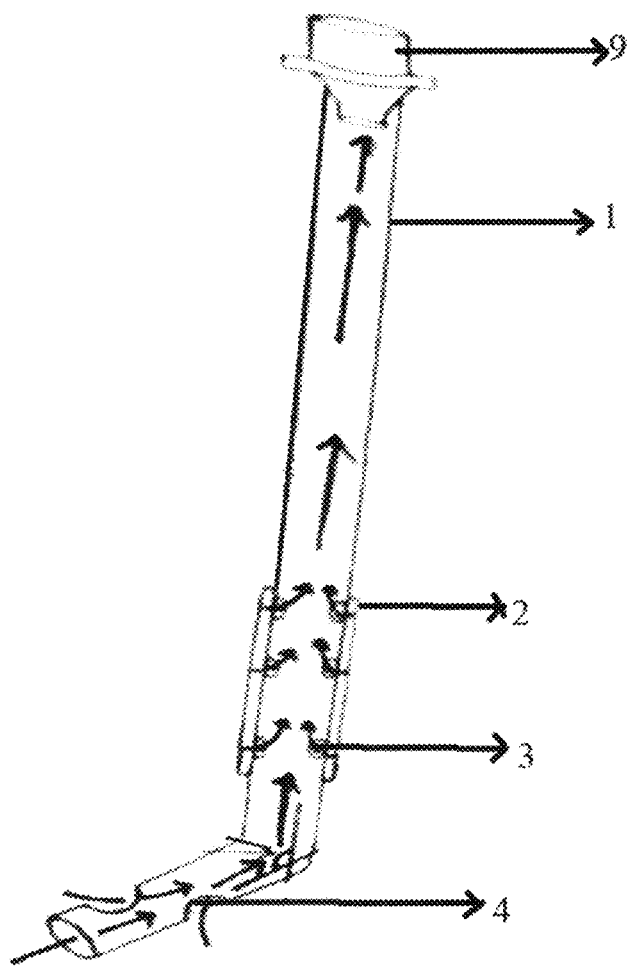
FIG. 7 shows the deflation of the dynamic cuff during the expiration. It also shows the neutral position of the distal flexible tip which is bent about 45 degree anteriorly.

A single embodiment of the invention has been described herein. Many a variation could be made without departing from the spirit of invention. Another invention pertaining to the same device is shown in FIGS. 1A and 1B:—
Where in, modified bougie, the distal tip (5a) is made flexible and attached via flexi-tip cord (6a) to a button (7a) with serrated markings (8a). These three black serrated markings on the body, help in achieving the desired angle of distal flexible tip. Where each marking above to previous corresponds to further bend of 10 degree. While the flexi-tip cord helps in flexing the distal tip at the predecided angle fixed by the serrated markings.

FIG. 1A is a longitudinal section of the modified bougie. It shows the different component of the apparatus which consists of body (1a), dynamic inflatable cuff (2a), inflation ports (3a), ventilation ports (4a), flexible distal tip (5a), button (7a) with serrated markings (8a), flexi tip cord (6a), universal connector (9a). It also shows the neutral position of the distal flexible tip which is at 45 degree anteriorly and corresponds to the +1 marking on the body FIG. 1B shows the distal flexible tip of the modified bougie at 10 degree anteriorly (over and above the 45 degree anteflexion) which corresponds to the +2 marking on the body, it helps in passing through the laryngeal inlet if it lies anteriorly.

Usually the neutral position of the distal tip in this modified bougie is 45 degree flexion which corresponds to the :+1" marking on the body.

Another invention pertaining to the same device is shown in FIGURE XX: This invention will aid in endobronchial tube placement and visual confirmation of the same. Where in, modified ventilating bougie, describe above, the distal end of the body, till the 35 cm mark, will be colored in such a way that, longitudinally, the Right half will be in one colour and the Left half will be in another colour of sufficient contrast (For ex: Right half of the tube can be white and Left half can be blue)

Another invention pertaining to the same device is shown in FIGURE XX, wherein the modified ventilating bougie will have a different colour in is proximal portion, that is beginning from the 35 cm mark till the proximal end. The appearance of this colour at the level of the lip will indicate that the distal end of the modified bougie is lying in the oesophagus and not in the trachea.

By virtue of the bent distal tip, which is bent at 45 degrees anteriorly, when the distal tip enters the Right bronchus, the Left half of the bougie will face anteriorly at the level of the lips, which can be immediately recognized by the colour code (i.e, Blue colour anteriorly at the mouth). The vice versa is true when the distal tip is placed at the Left bronchus (i.e, White colour anteriorly at the mouth). This will give a visual confirmation of the placement of the tip of the bougie in the desired bronchus. (FIG. NO. XX)

The body of the bougie will be marked in centimetres from the distal tip till the proximal tip. This will enable the physician to know how much of the bougie has entered the airway.

We claim:

1. A tracheal tube insertion facilitator having capability of ventilating a human or an animal, comprising:

a) an outer cylindrical member with a proximal end, a hollow body and a distal tip which is configured to bend forward;

wherein the outer cylindrical member near its distal tip houses one or more ventilation ports that is in fluid communication with an inner lumen of the outer cylindrical member allowing escape of ventilated gases into lungs;

a self-inflating dynamic cuff disposed on a portion of the outer cylindrical member, proximal to the ventilation ports, said self-inflating dynamic cuff including an inner surface being in fluid communication with the inner lumen of the outer cylindrical member through inflation ports and configured to mimic intraluminal pressures without any time lag or pressure gradient, thereby facilitating inflation of the self-inflating dynamic cuff during positive pressure ventilation (PPV) and jet ventilation;

b) a hollow metallic stylet with a proximal end, a hollow body and a distal end, the hollow metallic stylet being positioned in the inner lumen of the outer cylindrical member;

wherein the hollow metallic stylet is configured to support the outer cylindrical member and provide jet ventilation through an interior of the hollow metallic stylet;

wherein the body of the hollow metallic stylet houses one or more inflation apertures at a position enclosed by the self-inflating dynamic cuff; wherein the air from jet ventilation into the hollow metallic stylet, traverses through the inflation apertures to the inflation ports.

2. The tracheal tube insertion facilitator of claim 1, wherein the self-inflating dynamic cuff inflates during positive pressure ventilation and seals a tracheal lumen, thereby preventing the escape of respiratory gases to the nose and mouth, during an inspiratory phase of a respiratory cycle.

3. The tracheal tube insertion facilitator of claim 1, wherein the self-inflating dynamic cuff is configured to deflate during an expiratory phase of a respiratory cycle, and configured to allow expired gases to escape around the outer surface of the outer cylindrical member, and exit through nasal and oral cavities of the human or the animal.

4. The tracheal tube insertion facilitator of claim 1, wherein the body of the outer cylindrical member has vibration transmitting properties.

5. The tracheal tube insertion facilitator of claim 1, wherein the outer cylindrical member has markings starting from the distal tip till the proximal end, enabling identification of level of insertion.

6. The tracheal tube insertion facilitator of claim 1, wherein the outer cylindrical member is divided into a distal portion and a proximal portion about 35 centimeters from the distal tip.

7. The tracheal tube insertion facilitator of claim 6, wherein the proximal portion of the outer cylindrical member has a different color and texture than the distal portion of the outer cylindrical member.

8. The tracheal tube insertion facilitator of claim 6, wherein the distal portion of the outer cylindrical member is colored longitudinally in contrasting colors to demarcate the hollow body of the outer cylindrical member into a right half and a left half, enabling identification and accurate placement of the distal tip in the desired bronchus.

9. The tracheal tube insertion facilitator of claim 1, wherein the proximal end of the outer cylindrical member is connected to a specialized connector configured to create an airtight seal enabling positive pressure ventilation (PPV) or jet ventilation.

10. The tracheal tube insertion facilitator of claim 1, wherein the proximal end of the hollow metallic stylet is configured to work with a jet ventilation system.

\* \* \* \* \*